United States Patent [19]

Frank et al.

[11] Patent Number: 4,521,527

[45] Date of Patent: Jun. 4, 1985

[54] MOLDED IRON CATALYST AND ITS PREPARATION

[75] Inventors: Gerhard Frank, Hirschberg; Peter Rudolf, Neuhofen; Gerald Neubauer, Weinheim; Manfred Ohlinger, Frankenthal; Hans J. Wilfinger; Emil Pfannebecker, both of Schifferstadt; Paul Duffner, Ludwigshafen, all of Fed. Rep. of Germany

[73] Assignee: BASF Aktiengesellschaft, Fed. Rep. of Germany

[21] Appl. No.: 524,319

[22] Filed: Aug. 18, 1983

[30] Foreign Application Priority Data

Aug. 21, 1982 [DE] Fed. Rep. of Germany ....... 3231192

[51] Int. Cl.$^3$ ............... B01J 23/78; B01J 23/74; C07C 5/12; C07C 87/14
[52] U.S. Cl. ............... 502/184; 502/174; 502/185; 564/490; 564/492
[58] Field of Search ............... 502/185, 184, 183, 181, 502/174, 330, 338, 406, 150; 252/62.55; 564/492

[56] References Cited

U.S. PATENT DOCUMENTS

| | | | |
|---|---|---|---|
| 3,082,067 | 3/1963 | Hund | 23/200 |
| 3,232,888 | 1/1966 | Adam | 252/435 |
| 3,344,085 | 9/1967 | Isaks et al. | 502/185 |
| 3,758,584 | 9/1973 | Bivens et al. | 502/338 |
| 3,986,985 | 10/1976 | Dewdney et al. | 502/338 |
| 4,165,232 | 8/1979 | Jaeckh et al. | 252/62.55 |
| 4,295,879 | 10/1981 | Steck et al. | 252/62.55 |
| 4,310,349 | 1/1982 | Kahan et al. | 75/0.5 R |
| 4,426,342 | 1/1984 | Dria et al. | 502/150 |

FOREIGN PATENT DOCUMENTS

| | | |
|---|---|---|
| 1143390 | 2/1969 | United Kingdom . |
| 1317464 | 5/1973 | United Kingdom . |
| 1486890 | 9/1977 | United Kingdom . |

*Primary Examiner*—P. E. Konopka
*Attorney, Agent, or Firm*—Keil & Weinkauf

[57] ABSTRACT

Molded iron catalysts which contain metallic iron particles, obtained from anisometric iron oxide particles by contact with hydrogen at $\leq 500°$ C., and a lubricant, are prepared.

4 Claims, No Drawings

MOLDED IRON CATALYST AND ITS PREPARATION

The present invention relates to a molded iron catalyst containing metallic iron particles and a lubricant, and to its preparation.

In the preparation of amines by hydrogenating nitriles, eg. the preparation of hexamethylenediamine from adiponitrile, cobalt-containing catalysts are preferably used owing to their high selectivity. Such processes are disclosed in, for example, German Pat. Nos. 1,072,972 and 1,259,899. However, the life of the cobalt catalysts used no longer meets the technical requirements. Moreover, it has been found that, for reasons of industrial hygiene, it is advisable to avoid dusts of metallic cobalt and of its sparingly soluble compounds. Iron-containing catalysts have also been employed for the hydrogenation of nitriles to amines, but relatively high temperatures are required when these catalysts are used. This leads to increased formation of by-products, eg. azacycloheptane and the diamines, such as 2-aminomethylcyclopentylamine and 1,2-diaminocyclohexane, which are difficult to separate from the hexamethylenediamine, as well as to the formation of bishexamethylenetriamine and oligomers. For example, German Laid-Open Application DOS No. 2,429,293 discloses that magnetite can be melted and then reduced with hydrogen to give a catalyst which exhibits a selectivity with respect to hexamethylenediamine of from 98 to 99% at hot-spot temperatures of from 150° to 170° C. The contents of 1,2-diaminocyclohexane are, however, 0.2% by weight. The process which is described in German Published Application DAS No. 2,034,380, and in which the catalyst used is a granulated iron compound which is converted to metallic iron by reduction with hydrogen, also gives selectivities of only 97–98.8% by weight. Such iron catalysts do not yet satisfy all industrial requirements and therefore need to be improved.

It is an object of the invention to provide iron catalysts which, when used in the hydrogenation of nitriles to amines, have a long life, permit low hydrogenation temperatures, produce a small amount of byproducts and have a high selectivity.

We have found that this object is achieved by molded iron catalysts which contain metallic iron particles, obtained from anisometric iron oxides by contact with hydrogen at $\leq 500°$ C., and a lubricant.

The present invention furthermore relates to a process for the preparation of molded iron catalysts, wherein anisometric iron oxide particles are reduced with hydrogen, at from 250° to 500° C., to metallic iron particles, these are stabilized by treatment with a mixture of nitrogen and air, the stabilized iron particles are pressed together with a lubricant to form moldings and the latter are activated by treatment with hydrogen at $\leq 500°$ C.

The present invention furthermore relates to the use of the molded iron catalysts for the hydrogenation of organic nitriles to the corresponding amines.

The novel iron catalysts have the advantages of a long life, superior mechanical properties even after prolonged use and high selectivity at low temperatures. Moreover, the novel catalysts give fewer by-products which are difficult to separate from the desired products.

The novel catalytic material contains metallic iron particles obtained from anisometric, eg. acicular, iron oxide particles by contact with hydrogen at $\leq 500°$ C. Advantageously, the metallic iron particles exhibit a degree of reduction of $=95\%$. The degree of reduction is the amount of available iron, in %, which is present in metallic form.

Anisometric $\gamma$-iron oxides, in particular $\gamma$-iron (III) oxides and $\gamma$-iron(III) oxide hydrate, are preferably used. $\gamma$-iron(III) oxide hydrate, which is known under the name lepidocrocite, is particularly preferred, and can be obtained, for example, by the method described in German Published Application DAS No. 1,061,760. The anisometric iron oxides have a mean particle length of from 0.1 to 2 $\mu$m, preferaby from 0.2 to 1.2 $\mu$m, a length/width ratio of from 5:1 to 40:1 and a BET specific surface area of from 25 to 80 $m^2/g$. The products obtained by heating the stated iron(III) oxides may also be used, heating advantageously being carried out at from 250° to 700° C. The iron oxides used advantageously have an alkali content of less than 0.1% by weight, calculated as $Na_2O$.

The novel iron catalyst furthermore contains a lubricant, for example an inorganic substance with a lattice structure, such as talc or graphite. Advantageously, the catalysts contain from 1 to 5% by weight, based on the total catalytic material comprising iron particles and lubricant, of a lubricant. Graphite has proved a particularly useful lubricant. The novel iron catalyst therefore essentially consists of metallic iron particles obtained from an acicular iron oxide, small amounts of iron oxide, depending on the degree of reduction, and a lubricant.

The iron catalyst according to the invention is molded to give, for example, spheres, tablets or extrudates, and advantageously has an indentation hardness of $=300$ $kp/cm^2$.

The novel catalytic material is advantageously prepared from, for example, a $\gamma$-iron(III) oxide, in particular $\gamma$-iron(III) oxide hydrate (lepidocrocite). The products obtained by heating the stated iron(III) oxides may also be used, heating advantageously being carried out at from 250° to 700° C. $\gamma$-iron(III) oxide hydrate is obtained, for example, from an aqueous solution of an iron salt with sodium hydroxide solution by a process as described in German Published Application DAS No. 1,061,760. Advantageously, the $\gamma$-iron oxide hydrate particles are washed until the alkali content is less than 0.1% by weight, calculated as $Na_2O$.

The acicular iron(III) oxide particles are reduced with hydrogen in a fluidized bed, a rotary furnace or, preferably, in a stirred fixed bed at from 260° to 500° C., in particular from 300° to 450° C., in the course of from 3 to 36 hours. It is advantageous to use a stream of dry hydrogen, a relatively high flow velocity being maintained. It has proved useful to use not less than a 60-fold excess of hydrogen. Advantageously, reduction is carried out until the degree of reduction is $\geq 95\%$. The resulting acicular metal particles, which essentially consist of iron, substantially retain the shape of the starting materials, and are homogeneous in spite of having been subjected to a conversion reaction.

The metal particles are then stabilized. This is the procedure in which the metal particles are coated with an oxide layer, by means of controlled oxidation, in order to eliminate the pyrophoricity resulting from the large free surface area of the small particles. This is achieved by passing an air/nitrogen mixture over the metal powder while exactly maintaining a temperature which is preferably not more than 100° C., in particular not more than 80° C. After stabilization, the degree of reduction should be no less than 80%, preferably no less than 90%. The stabilized iron particles have a BET surface area of from 4 to 25, preferably from 8 to 12, m²/g, lengths of from 0.05 to 2.0 μm and pore volumes of less than 0.4 cm³/g, and the ratio of micropores to macropores is from 1:6 to 1:10, macropores therefore predominating. The stabilized particles are anisotropic.

The stabilized iron particles obtained in this manner are mixed with an inert lubricant, preferably graphite. It is advantageous to use from 2 to 5% by weight of lubricant. The mixture of stabilized iron particles and lubricant is advantageously converted to moldings, eg. tabletted, under a nitrogen atmosphere. The indentation hardness of the moldings should be ≦300 kp/cm².

The resulting moldings are activated by treatment with a relatively large (eg. 60-fold) excess of hydrogen at ≦500° C., preferably from 300° to 360° C., under atmospheric pressure or superatmospheric pressure, eg. from 100 to 150 bar. In this procedure, the degree of reduction achieved is advantageously ≧95%. The activation increases the indentation hardness of the moldings, for example from 300 to 600–800 kp/cm².

The molded iron catalysts according to the invention have a high activity which permits hydrogenation to be carried out at below 120° C., whereas prior art procedures require hot-spot temperatures as high as 150° C. and above. A striking feature is their low tendency to form undesirable cyclic by-products; for example, in the preparation of hexamethylenediamine, the concentrations of 1,2-diaminocyclohexane and azacycloheptane are substantially less than 0.2% and the concentration of 2-aminomethylcyclopentylamine is less than 0.002%. The novel catalyst also has high mechanical stability; this can be achieved by carrying out the molding procedure not at the stage of the anisometric iron(III) oxide but only after the latter has been reduced to metallic iron particles and subsequently stabilized. If moldings are prepared from anisometric iron(III) oxide and a lubricant and the moldings are then reduced, their indentation hardness decreases, for example from 300 kp/cm² to 25 kp/cm² when the degree of reduction reaches 95%. The time-on-stream of the resulting catalyst is less than 100 days. Both the reduction temperature and the hydrogenation temperature are higher than in the case of the process according to the invention, while the selectivity is substantially lower.

The novel catalysts can be advantageously used for hydrogenating organic nitriles to the corresponding amines.

The catalyst according to the invention is particularly useful for the preparation of alkylamines and alkylenediamines by reacting an alkanenitrile or an alkanedinitrile of 3 to 18 carbon atoms with hydrogen in the presence of ammonia. The novel catalysts are particularly important for the preparation of hexamethylenediamine by reacting adiponitrile with hydrogen in the presence of ammonia. This process is carried out at from 80° to 140° C., preferably from 110° to 120° C., and under a pressure of from 100 to 400, preferably from 200 to 300, bar. The hydrogenation is advantageously carried out in the presence of ammonia, but some of this may be replaced by recycled crude hydrogenation mixture, which essentially consists of hexamethylenediamine and ammonia. It has proved useful for the volume ratio of adiponitrile to ammonia to be from 1:2 to 1:20, preferably from 1:6 to 1:12.

The Examples which follow illustrate the invention.

EXAMPLE 1

Preparation of the catalyst 600 kg of acicular lepidocrocite (γ-FeOOH), prepared as described in German Published Application DAS No. 1,061,760 and having a chlorine content of <0.1%, an Na₂O content of <0.1%, a specific surface area of 32 m²/g, a mean needle length of 0.8 μm, a length/width ratio of the needles of 22:1, a bulk density of 0.37 g/cm³ and a pH of 7.2, are reduced to metallic iron (Fe≧95%) with 400 m³(S.T.P.)/hour of hydrogen for 38 hours at 400° C. in a stirred fixed bed (stoichiometric hydrogen excess: 64). The pyrophoric acicular metallic pigment is then provided with a stabilizing oxide layer at 60° C. in a nitrogen/air mixture, and the degree of reduction should not fall below 90%. The yield is 400 kg. The saturation magnetization of the iron particles is 153 nT m³/g in a magnetic field of 160 kA/M. The iron particles have a specific surface area of 7.2 m²/g (measured by the BET method), and electron microscope photographs show that they possess an anisotropic geometrical shape (acicular or rod-like).

To prepare molded materials having a diameter of 5 mm and a height of 4 mm, the stabilized pulverulent metallic pigment is mixed with 2% by weight of graphite and the mixture is tabletted under a nitrogen atmosphere. The indentation hardness of the tablets should not be less than 300 kp/cm².

EXAMPLE 2

350 liters of the moldings prepared as described in Example 1 are introduced into a reactor having a length of 1,800 mm and an internal diameter of 160 mm, and the moldings are treated with a large excess of hydrogen at 360° C. and under 150 bar for 24 hours in order to activate them. The hydrogen is circulated via a condenser in order to separate off water formed during the reduction.

After the catalyst has been cooled, the reactor is charged, using a trickling procedure and under a hydrogen pressure of 270 bar, with a mixture of 85 liters/hour of adiponitrile and 510 liters/hour of liquid ammonia, the hydrogen being circulated at a rate of 400 m³(S.T.P.)/hour. The temperature of the feed mixture is 78° C. and that at the reactor exit is 110° C.; the maximum hot-spot temperature is 119° C.

After ammonia has been evaporated off from the hydrogenation mixture, gas chromatographic analysis shows that the crude hexamethylenediamine comprises 0.02% by weight of hexylamine, 0.09% by weight of azacycloheptane, 0.11% by weight of 1,2-diaminocyclohexane and 99.78% by weight of hexamethylenediamine, as well as <0.01% of aminocapronitrile. The distillation residue, which predominantly consists of bishexamethylenetriamine, corresponds to 0.36%. The selectivity with respect to hexamethylenediamine is 99.4%. The activity and selectivity of the catalyst was unchanged after a time-on-stream of 400 days and without any regeneration.

EXAMPLE 3

In the reactor described in Example 2, 70 liters/hour of adiponitrile in 430 liters/hour of liquid ammonia and 490 liters/hour of recycled hydrogenation mixture are converted to hexamethylenediamine over the catalyst prepared as described in Example 1. Hydrogen is circulated at the rate of 350 m³(S.T.P.)/hour, and its pressure is maintained at 250 bar. Complete conversion of the adiponitrile is achieved, at a feed temperature of 77° C.; the temperature at the reactor exit is 104° C. and the maximum temperature in the reactor is 109° C.

Gas chromatographic analysis of the crude hexamethylenediamine after the ammonia has been evaporated off gives the following result: 0.01% of hexylamine, 0.05% of azacycloheptane, 0.11% of 1,2-diaminocyclohexane, 0.002% of 2-aminomethylcyclopentylamine, 99.80% of hexamethylenediamine and 0.01% of aminocapronitrile. The distillation residue corresponds to 0.40%, and the selectivity with respect to hexamethylenediamine is 99.44%.

EXAMPLE 4

3 liters of the catalyst prepared as described in Example 1 are introduced into a high-pressure reactor having a length of 2,000 mm and an internal diameter of 45 mm, and the catalyst is activated as described in Example 2. 100 ml/hour of adiponitrile and 1,200 ml/hour of liquid ammonia are metered into the reactor. At a hydrogenation temperature of 109° C. and under a pressure of 260 bar, the selectivity with respect to hexamethylenediamine is 99.3%. The crude hexamethylenediamine contains only 0.04% of azacycloheptane and 0.09% of 1,2-diaminocyclohexane. The distillation residue corresponds to 0.23%.

EXAMPLE 5

In a 2 liter shaken autoclave, 80 g of 2-methylglutarodinitrile and 1,000 ml of liquid ammonia are hydrogenated under 260 bar and at 100° C. in the presence of 80 g of catalyst tablets prepared as described in Example 1, hydrogenation being continued until hydrogen is no longer absorbed. For complete conversion of the dinitrile employed, the selectivity with respect to 2-methylpentamethylenediamine is 98.8%.

Using a similar procedure and under the above hydrogenation conditions, propionitrile in liquid ammonia is hydrogenated to n-propylamine with a selectivity of 97.5%.

EXAMPLE 6

The procedure described in Example 4 is followed, except that 3 liters of a catalyst prepared by tabletting a mixture of 98% of γ-FeOOH and 2% of graphite are used. The catalyst is reduced with hydrogen at 450° C. and under atmospheric pressure for 72 hours. The degree of reduction achieved is 95%. For complete conversion of 400 g/hour of adiponitrile in 1,460 g/hour of NH₃, a hydrogenation temperature of 155° C. and a pressure of 260 bar are required (trickling procedure).

The selectivity of the catalyst is 97.15% with respect to hexamethylenediamine. The crude hexamethylenediamine contains 1.56% of products from conversion reactions which have proceeded beyond the desired stage, and 1.29% of cyclic products (1,2-diaminocyclohexane and azacycloheptane).

EXAMPLE 7

The procedure described in Example 4 is followed, except that 3 liters of a catalyst are used which is obtained by reducing α-FeOOH, passivating the surface of the resulting metallic iron pigment, mixing the product with 2% of graphite and tabletting the mixture. The α-FeOOH is precipitated in an alkaline medium, so that the catalyst contains 0.18% of sodium hydroxide.

In the reactor, the catalyst is activated by treating it with hydrogen for 24 hours at 360° C. and under atmospheric pressure. 400 g/hour of adipodinitrile and 1,460 g/hour of NH₃ are then metered in by a trickling procedure.

Complete conversion of the adiponitrile is achieved at 172° C. The selectivity with respect to hexamethylenediamine is 97.8%, and 1.3% of cyclic byproducts and 0.8% of products from conversion reactions which have gone beyond the desired stage (predominantly bishexamethylenetriamine) are obtained.

We claim:

1. A molded iron catalyst having an indentation hardness greater than 300 kp/cm² which consists essentially of metallic iron particles having a degree of reduction of $\geq$95% and obtained from anisometric γ-iron oxide particles by contact with hydrogen at $\leq$500° C., and 1 to 5% by weight of graphite as a lubricant.

2. The catalytic material of claim 1, wherein the iron oxide used contains less than 0.1% by weight, calculated as sodium oxide, of alkali.

3. The catalytic material of claim 1, wherein the starting material used is anisometric γ-iron(III) oxide hydrate.

4. A process for the preparation of a molded iron catalyst comprising the following steps:
   (a) reducing anisometric γ-iron oxide particles with hydrogen at from 250° to 500° C. to metallic iron particles having a degree of reduction of $\geq$95%;
   (b) stabilizing the metallic iron particles by treatment with a mixture of air and nitrogen while maintaining a temperature of not more than 100° C. and achieving a degree of reduction of not less than 80%;
   (c) pelletizing the stabilized metallic iron particles together with 1 to 5% by weight of graphite to form moldings; and
   (d) activating said moldings by treatment with hydrogen at $\leq$500° C. achieving a degree of reduction of $\geq$95%.

* * * * *